United States Patent
Pearcey

(12) 
(10) Patent No.: US 6,427,697 B1
(45) Date of Patent: Aug. 6, 2002

(54) BELT AND METHOD FOR INCREASING COMFORT AND REDUCING BACK PAIN WHILE LYING DOWN

(76) Inventor: Mary Annette Pearcey, 2646 22nd St., Sarasota, FL (US) 34234

( * ) Notice: Subject to any disclaimer, the term of this patent is extended or adjusted under 35 U.S.C. 154(b) by 0 days.

(21) Appl. No.: 09/207,174

(22) Filed: Dec. 8, 1998

Related U.S. Application Data

(63) Continuation-in-part of application No. 09/058,659, filed on Jun. 22, 1998, now abandoned.

(51) Int. Cl.[7] .................................................. A61F 5/37
(52) U.S. Cl. ................. 128/876; 602/19; 2/338
(58) Field of Search .................. 128/869, 875, 128/876; 602/19; 2/311, 319, 322, 328

(56) References Cited

U.S. PATENT DOCUMENTS

| | | | | |
|---|---|---|---|---|
| 1,483,192 A | * | 2/1924 | Langgons | 2/338 |
| 3,001,202 A | * | 9/1961 | Serrano | 2/338 |
| 3,458,878 A | * | 8/1969 | Combs | 128/876 |
| 4,472,839 A | * | 9/1984 | Johansen | 2/338 |
| 4,552,135 A | | 11/1985 | Racz | |
| 4,694,772 A | | 9/1987 | Faulconer | |
| 4,778,307 A | | 10/1988 | Faulconer | |
| D300,340 S | | 3/1989 | Faulconer | |
| 4,810,134 A | | 3/1989 | Eaulconer | |
| 4,990,115 A | | 2/1991 | Vorhauer | |
| 4,991,573 A | * | 2/1991 | Miller | 602/192 |
| 5,046,894 A | | 9/1991 | Bergstrom | |
| 5,249,890 A | | 10/1993 | Bergstrom | |
| 5,651,763 A | * | 7/1997 | Gates | 602/19 |

OTHER PUBLICATIONS

Printout of "Mr. Diver, Inc." web page (http://www.mrdiver.cob/bcs.htm).

* cited by examiner

*Primary Examiner*—Michael A. Brown
(74) *Attorney, Agent, or Firm*—Banner & Witcoff, Ltd.

(57) ABSTRACT

The invention comprises a flexible padded belt adapted to be worn by a person when in a substantially horizontal position. The invention further comprises a method of reducing back pain and increasing comfort by wearing a flexible padded belt while lying down. The belt encircles the wearer's lower lumbar, side and abdominal regions, and fastens over the wearer's stomach. Padding in the portions of the belt contacting the wearer's sides and lower back support the wearer's spine and reduce spinal curvature when the wearer lies on his or her side, thereby promoting comfort and reducing pain. When the wearer lies on his or her back, the belt supports the lower lumbar region.

56 Claims, 3 Drawing Sheets

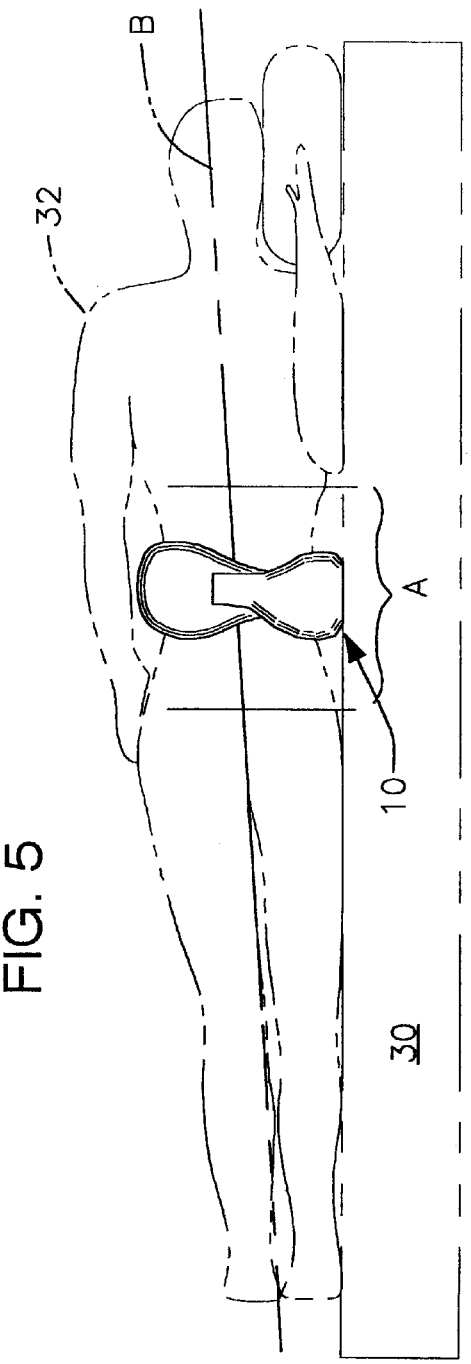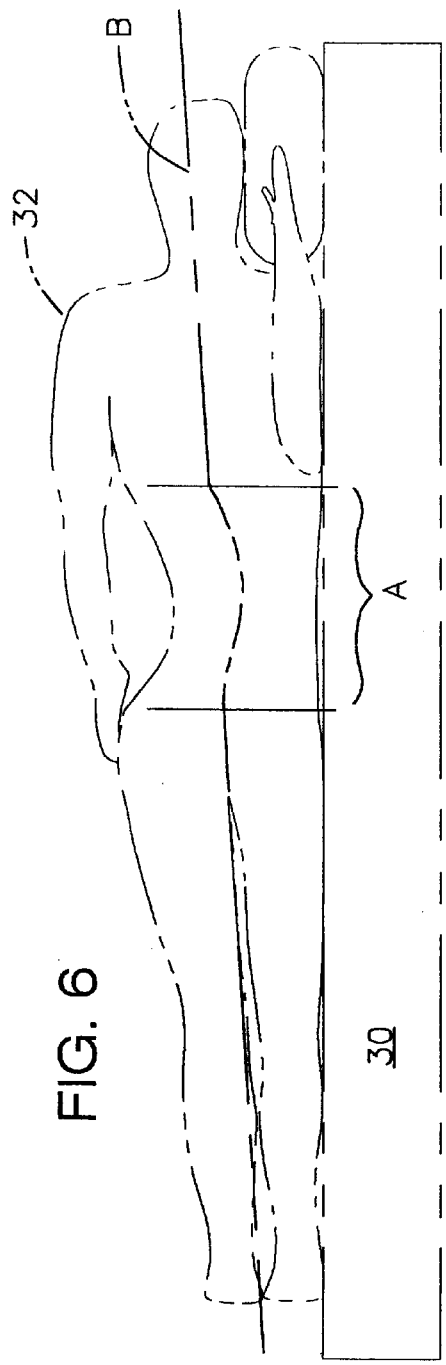

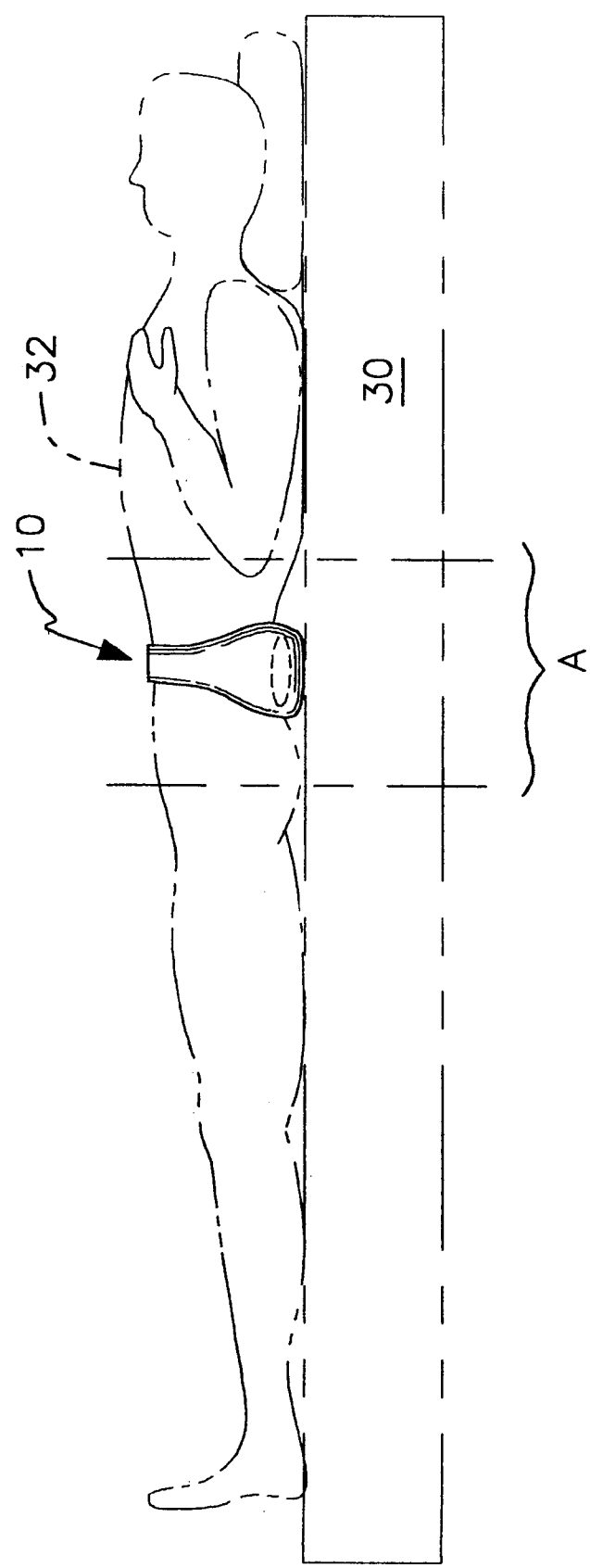

BELT AND METHOD FOR INCREASING COMFORT AND REDUCING BACK PAIN WHILE LYING DOWN

CROSS-REFERENCE TO RELATED APPLICATIONS

This is a Continuation-in-Part of application Ser. No. 09/058,659, filing date Jun. 22, 1998, now abandoned.

BACKGROUND OF THE INVENTION

During or after sleep, or other periods of lying in a horizontal position, some individuals experience discomfort in the lower back area. This invention relates to device and method for comfortably supporting the lower back and reducing spinal curvature when the wearer is lying in a substantially horizontal position on his or her side, thereby promoting wearer comfort and preventing back pain.

There are numerous prior art examples of belts designed to provide lower back support during lifting or other strenuous activity. For example, Gates, U.S. Pat. No. 5,651,763, discloses a belt with an incorporated stiff orthopedic pad that is intended to support the lower back. Rise, U.S. Pat. No. 5,421,809, discloses a two-piece belt for supporting the lower back and related muscles during activity. However, these belts rely, at least in part, upon intra-abdominal pressure within the belts (such as may be generated during lifting or other activity) to provide back and muscle support, and would not be suitable for supporting the lower back when the wearer is relaxed and in a substantially horizontal position. Racz, U.S. Pat. No. 4,552,135, discloses a belt designed to provide lower back support while the wearer is sitting (driving), but does not suggest back support while lying down and turned on one's side.

SUMMARY OF THE INVENTION

A padded belt is worn around an individual's midsection. The belt is filled with cushioning material in the portions contacting the user's lower back and sides. In the preferred embodiment, the thickness of said padding is approximately equal throughout most of the belt, but is substantially reduced or absent in the ends of the belt that fasten over the wearer's stomach. Normal filling thickness is approximately 1 inch per 72 pounds of body weight of the intended wearer, but belts can be manufactured with differing thicknesses to accommodate differing personal preferences and body types. The belt is widest in the portion that contacts the user's lower back, and the widths of the belt portions encircling the user's sides taper towards the front, where the belt is fastened over the user's stomach with hook and pile fastening material.

In use, the wearer fastens the belt around his or her lower back, sides and stomach. Although it can be varied based upon individual preference, the belt is normally worn in a snug, but not tight, fit. When lying on his or her side, the wearer's midsection rests on the belt's padding and is supported. When the user lies on his or her back, the wider portion of the belt fits comfortably into and supports the lower back.

The following detailed description and accompanying drawings provide a fuller understanding of the nature and advantages of the invention.

BRIEF DESCRIPTION OF THE DRAWINGS

FIG. 5 is a side elevational view of an individual (in phantom lines) wearing the belt and lying on his or her side;

FIG. 6 is a side elevational view of an individual lying on his or her side without the belt; and FIG. 7 is a side elevational view of an individual (in phantom lines) wearing the belt and lying on his or her back.

DESCRIPTION OF THE PREFERRED EMBODIMENT

Figure 1:
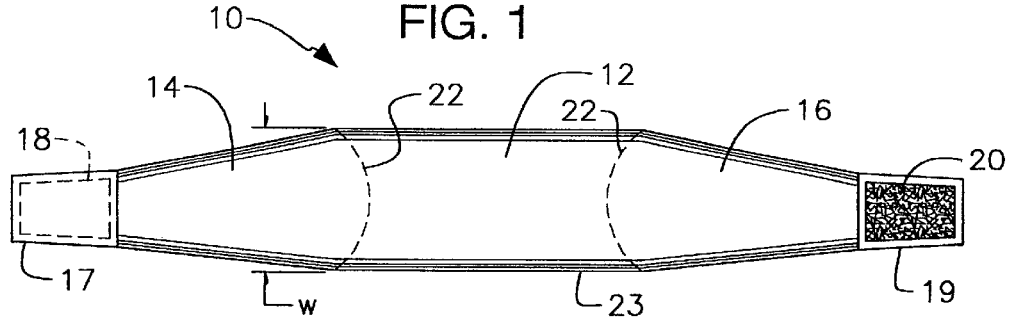
FIG. 1 is an elevational view of the inside of the belt when opened and stretched to its full length.
Figure 2:
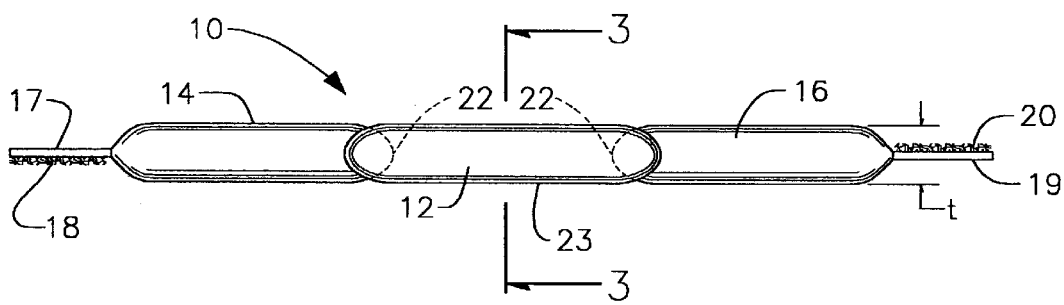
FIG. 2 is a view of the bottom edge of the belt when opened and stretched to its full length.
Figure 4:
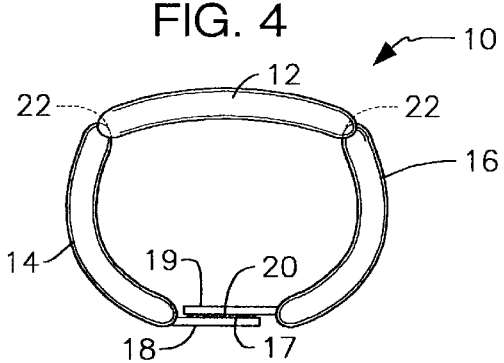
FIG. 4 is a top view of the belt when fastened.

Referring to the drawings, FIGS. 1 and 2 show a flexible padded belt 10. The belt 10 has central portion 12 of width w. Side portions 14 and 16 are located on opposite sides of central portion 12, and with central portion 12, form belt 10 as a continuous unit. The central portion 12 and side portions 14 and 16 are constructed from material or materials that provide cushioned support while maintaining flexibility. Side portions 14 and 16 each have a free end (17 and 19, respectively). Affixed to free ends 17 and 19 are fastening means 18 and 20 (hook and pile fastener material, commonly sold under the name VELCRO) for fastening ends 17 and 19 together. Although the preferred embodiment employs hook and pile material as the fastening means, other types of fastening means may be used (for example, laces, traditional belt buckle, snaps, etc.). FIG. 4 shows the belt in a closed position with ends 17 and 19 fastened together with hook and pile fastener 18 and 20. In use, belt 10 is wrapped around an individual's lower back and sides and fastened over the stomach, as shown in FIG. 5.

Figure 3:
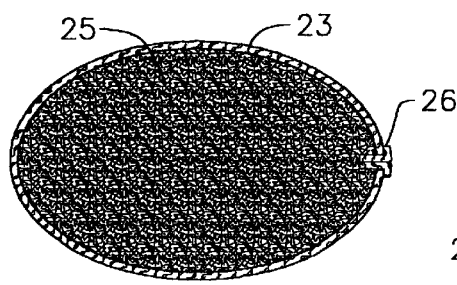
FIG. 3 is an enlarged sectional view of the belt showing the belt's outer covering, padding and stitching.

The belt 10 can be constructed from any combination of materials that provides cushioned support, but at the same time remains sufficiently flexible to allow belt 10 to curve around a wearer's lower back, sides and stomach. FIGS. 1, 2 and 3 show the preferred embodiment comprising a fabric panel 23 that is folded over on its lengthwise dimension to form the outer covering of belt 10. Panel 23 is wrapped around a layer of padding 25, and its edges are then sewn together with stitching 26 as shown in FIG. 3. To prevent shifting of padding 25 within belt 10, 2 curved stitches 22 are sewn through both sides of folded over panel 23. Said curved stitches effectively separate side portions 14 and 16 from central portion 12. However, said curved stitches 22 permit belt 10, when wrapped around a wearer's lower back, sides and stomach, to present a continuous padded surface around the wearer's sides and lower back.

Side panels 14 and 16 taper from their connections to central portion 12 (where the side panels are widest) towards the ends 17 and 19 (where the side panels are narrowest). Padding thickness t is approximately constant throughout the belt's length. However, the padding is substantially reduced or absent from the end regions of the side portions. In this manner, the belt thickness is minimized over the wearer's stomach, where padding is typically not required.

In the preferred embodiment, central portion 12 width w is between five and eight inches, and may be somewhat wider in the center portion of central portion 12 (i.e., midway between two curved stitches 22) (not shown in drawings). However, width w can be varied, and is constrained at the upper range by the size of the wearer's body. As shown in FIG. 5, the belt is intended to fit in the midsection region A of the body located generally between the hips and lower chest. Width w must not be so great that the belt 10 extends appreciably outside midsection region A. At the other extreme, central portion width w cannot be so small that the belt fails to provide adequate supporting surface area along the part of the wearer's body in contact with the belt, or to otherwise cause discomfort. In the preferred embodiment, side panels 14 and 16 are tapered for added wearer comfort. Panel 23 can be made from any type of fabric desired. Readily available materials such as 100% cotton or a cotton/lined blend (preferably 70% cotton/30% linen) offer the advantages of low cost, durability and easy laundering, and provide a comfortable feeling next to the skin. Any type of padding material that provides soft but supportive cushioning can be used, such as 100% polyester fiber. The padding firmness can be adjusted during manufacture to accommodate differing personal preferences, body weights, or body types (i.e., the wearer's shape and amount of body fat). In the preferred embodiment, for a belt sized for a person weighing between 151 to 180 pounds, with folded-over panel 23 having, prior to insertion of padding 25, a central portion 12 width w of approximately 7.7 inches and a padded length (i.e., the entire belt length except for the area covered by hook and pile fastening means 18 and 20) of approximately 33.5 inches, filling the belt with approximately 6 to 7 ounces of 100% polyester fiber padding (such as that sold under the trade name POLY-FIL by Fairfield Processing Corporation) evenly distributed along the belt's padded length will provide the required firmness. However, the thickness and firmness of the padding can be varied, as long as the padding is not so thick or firm that it pushes the wearer's midsection too far upward or otherwise causes user discomfort. At the other extreme, the padding can not be so thin or yielding that it provides no noticeable support for the wearer's midsection.

FIG. 5 shows belt 10 in use. A wearer 32 places the belt around his or her lower back and sides and fastens it over the stomach. As the wearer 32 lies on his or her side on a bed or other surface 30, the belt 10 rests comfortably in midsection region A which is approximately between the wearer's hips and lower chest. Belt 10 supports the wearer's midsection region A and lifts it slightly in the direction above the plane of lying surface 30. By so doing, the wearer's body centerline B is maintained in a more or less straight posture. By way of contrast, FIG. 6 shows a person 32 lying on the same surface 30 without wearing belt 10. As shown in FIG. 6, the midsection region A of person 32 is no longer supported, and moves closer to or into contact with lying surface 30. As a result, body centerline B is not as straight, ultimately leading to discomfort. Although the stiffness of lying surface 30 shown in FIGS. 5 and 6 is exaggerated to more clearly show the belt's operation, and although many mattresses or other lying surfaces might conform somewhat to a person's body shape, a person lying on a softer or more conformal surface would still experience body centerline distortion without additional support in midsection region A. The amount of padding 25 and belt thickness t can be adjusted during manufacture to accommodate different levels of mattress firmness. The amount by which an individual's midsection would conform to the lying surface without wearing belt 10 is also exaggerated somewhat in FIG. 6 for clarity.

By comfortably fitting within the wearer's lower back region, central portion 12 also supports and comforts the wearer when he or she lies on his or her back, as shown in FIG. 7. Because there is normally a slight hollow in the lower back, the central portion 12 of belt 10 supports and helps maintain this natural slight hollow when the wearer lies on his or her back. Additionally, the padding of central portion 12 provides more stiffness along the belt's length than would be provided by an unpadded portion, and thereby serves to keep side portions 14 and 16 in place without wearing belt 10 excessively tight. Otherwise, side portions 14 and 16 might shift as the wearer turns over during sleep. The belt 10 provides the added advantage of not requiring continued adjustment as the wearer turns from one side to the other, as would be necessary if a person were trying to obtain the same type of support with a pillow or other device not attached to the body.

The above description is of a preferred embodiment of the invention. However, the invention is not limited by the embodiment described, and includes modifications to and variations upon the materials, dimensions and characteristics described.

I claim:

1. A belt for supporting a wearer's lower back while lying in a substantially horizontal position, said belt comprising:

a flexible central portion sized to fit over the wearer's lower lumbar region, said central portion having two opposing ends, said central portion having padding of a sufficient thickness and firmness to support the wearer's lower lumbar region by lifting only said lower lumbar region from a substantially horizontal lying surface;

a flexible first side portion, said first side portion having a free end and an attached end, said attached end being joined to one of the opposing ends of said central portion, said first side portion having padding of a sufficient thickness and firmness to support a side region of the wearer's body, said side region located generally between said wearer's hips and lower chest, by lifting only said side region from a substantially horizontal lying surface;

a flexible second side portion, said second side portion having a free end and an attached end, said attached end being joined to the other opposing end of said central portion, said second side portion having padding of a sufficient thickness and firmness to support an opposite side region of the wearer's body, said opposite side region located generally between said wearer's hips and lower chest, by lifting only said opposite side region from a substantially horizontal lying surface; and fastening means attached to the free ends of said first and second side portions for holding said central portion, first side portion and second side portion in a position encircling the wearer's lower lumbar, side and abdominal regions.

2. The belt of claim 1 wherein the regions surrounding the free ends of said first and second side portions are substantially less padded than the regions surrounding the attached ends of said first and second side portions.

3. The belt of claim 2 wherein said central portion has an uncompressed thickness of approximately one inch per seventy-two pounds of wearer body weight.

4. A method of preventing back discomfort comprising wearing the belt of claim 3 while lying in a substantially horizontal position.

5. The belt of claim 2 wherein said first and second side portions taper along their length from wider widths at the attached ends of said first and second side portions to narrower widths at the free ends of said first and second side portions.

6. The belt of claim 4 wherein said central portion is between five and eight inches wide.

7. A method of preventing back discomfort comprising wearing the belt of claim 6 while lying in a substantially horizontal position.

8. A method of preventing back discomfort comprising wearing the belt of claim 5 while lying in a substantially horizontal position.

9. A method of preventing back discomfort comprising wearing the belt of claim 2 while lying in a substantially horizontal position.

10. A method of preventing back discomfort comprising wearing the belt of claim 1 while lying in a substantially horizontal position.

11. The belt of claim 1 wherein the uncompressed thickness of said padding in said central and side portions is at least 1 inch.

12. A method of preventing back discomfort comprising wearing the belt of claim 11 while lying in a substantially horizontal position.

13. The belt of claim 1 wherein the uncompressed thickness of said padding in said central and side portions is at least 1½ inches.

14. The belt of claim 1 wherein the uncompressed thickness of said padding in said central and side portions is at least 2 inches.

15. A method of preventing back discomfort comprising wearing the belt of claim 14 while lying in a substantially horizontal position.

16. The belt of claim 1 wherein the uncompressed thickness of said padding in said central and side portions is at least 2½ inches.

17. The belt of claim 1 wherein the uncompressed thickness of said padding in said central and side portions is at least 3 inches.

18. A method of preventing back discomfort comprising wearing the belt of claim 17 while lying in a substantially horizontal position.

19. The belt of claim 1 wherein the uncompressed thickness of said padding in said central and side portions is at least 3½ inches.

20. The belt of claim 1 wherein the uncompressed thickness of said padding in said central and side portions is at least 4 inches.

21. A method of preventing back discomfort comprising wearing the belt of claim 20 while lying in a substantially horizontal position.

22. A belt for increasing comfort and reducing back pain while lying down, comprising:
  a flexible padded belt for supporting only a wearer's midsection, said midsection located generally between said wearer's hips and lower chest, while said wearer is lying in a substantially horizontal position;
  said flexible padded belt sized to encircle the wearer's lower back, side and stomach regions;
  said flexible padded belt having padding of a firmness and thickness sufficient to maintain the wearer's lower back in a substantially straight posture when said belt is situated between said wearer's side and a substantially horizontal lying surface and sufficient to maintain the natural hollow of the wearer's lower back region when said belt is situated between said wearer's lower back region and a substantially horizontal lying surface; and
  said flexible padded belt having two ends, said ends further having fastening means for holding said flexible padded belt in a position encircling the wearer's lower back, side and stomach regions without leaving significant excess unsecured length, wherein
  said belt tapers from a greater width in the portion of the belt adapted to support the wearer's lower back to a lesser width in the two free ends;
  the regions of said flexible padded belt proximate to said free ends have substantially reduced padding; and
  the thickness of said padding is approximately one inch per seventy-two pounds of body weight of an intended wearer.

23. A method of preventing back discomfort comprising wearing the belt of claim 22 while lying in a substantially horizontal position.

24. A belt for increasing comfort and reducing back pain while lying down, comprising:
  a flexible padded belt for supporting only a wearer's midsection, said midsection located generally between said wearer's hips and lower chest, while said wearer is lying in a substantially horizontal position;
  said flexible padded belt sized to encircle the wearer's lower back, side and stomach regions;
  said flexible padded belt having padding, said padding extending along a substantial length of the belt, of a firmness and thickness sufficient to maintain the wearer's lower back in a substantially straight posture when said belt is situated between said wearer's side and a substantially horizontal lying surface and sufficient to maintain the natural hollow of the wearer's lower back region when said belt is situated between said wearer's lower back region and a substantially horizontal lying surface; and
  said flexible padded belt having two ends, said ends further having fastening means for holding said flexible padded belt in a position encircling the wearer's lower back, side and stomach regions without leaving significant excess unsecured length,
wherein the uncompressed thickness of said padding in the portions of said belt intended to contact the wearer's sides and lower back is at least 1 inch.

25. The belt of claim 24 wherein the uncompressed thickness of said padding in the portions of said belt intended to contact the wearer's sides and lower back is at least 1½ inches.

26. The belt of claim 24 wherein the uncompressed thickness of said padding in the portions of said belt intended to contact the wearer's sides and lower back is at least 2 inches.

27. A method of preventing back discomfort comprising wearing the belt of claim 24 while lying in a substantially horizontal position.

28. A method of preventing back discomfort comprising wearing the belt of claim 26 while lying in a substantially horizontal position.

29. The belt of claim 24 wherein the uncompressed thickness of said padding in the portions of said belt intended to contact the wearer's sides and lower back is at least 2½ inches.

30. The belt of claim 24 wherein the uncompressed thickness of said padding in the portions of said belt intended to contact the wearer's sides and lower back is at least 3 inches.

31. A method of preventing back discomfort comprising wearing the belt of claim 30 while lying in a substantially horizontal position.

32. The belt of claim 24 wherein the uncompressed thickness of said padding in the portions of said belt intended to contact the wearer's sides and lower back is at least 3½ inches.

33. The belt of claim 24 wherein the uncompressed thickness of said padding in the portions of said belt intended to contact the wearers sides and lower back is at least 4 inches.

34. A method of preventing back discomfort comprising wearing the belt of claim 33 while lying in a substantially horizontal position.

35. A belt for increasing comfort and reducing back pain while lying down, comprising:
   a flexible padded belt for supporting only a wearer's midsection, said midsection located generally between said wearer's hips and lower chest, while said wearer is lying in a substantially horizontal position;
   said flexible padded belt sized to encircle the wearer's lower back, side and stomach regions;
   said flexible padded belt having padding, said padding extending along a substantial length of the belt, of a firmness and thickness sufficient to maintain the wearer's lower back in a substantially straight posture when said belt is situated between said wearer's side and a substantially horizontal lying surface and sufficient to maintain the natural hollow of the wearer's lower back region when said belt is situated between said wearer's lower back region and a substantially horizontal lying surface; and
   said flexible padded belt having two ends, said ends further having fastening means for holding said flexible padded belt in a position encircling the wearer's lower back, side and stomach regions without leaving significant excess unsecured length,
   wherein said flexible padded belt is a single piece, and wherein the uncompressed thickness of said padding in the portions of said belt intended to contact the wearer's sides and lower back is at least 1 inch.

36. The belt of claim 35 wherein the uncompressed thickness of said padding in the portions of said belt intended to contact the wearer's sides and lower back is at least 1 inch.

37. The belt of claim 35 wherein the uncompressed thickness of said padding in the portions of said belt intended to contact the wearer's sides and lower back is at least 1½ inches.

38. The belt of claim 35 wherein the uncompressed thickness of said padding in the portions of said belt intended to contact the wearer's sides and lower back is at least 2 inches.

39. The belt of claim 35 wherein the uncompressed thickness of said padding in the portions of said belt intended to contact the wearer's sides and lower back is at least 2½ inches.

40. The belt of claim 35 wherein the uncompressed thickness of said padding in the portions of said belt intended to contact the wearer's sides and lower back is at least 3 inches.

41. The belt of claim 35 wherein the uncompressed thickness of said padding in the portions of said belt intended to contact the wearer's sides and lower back is at least 3½ inches.

42. The belt of claim 35 wherein the uncompressed thickness of said padding in the portions of said belt intended to contact the wearer's sides and lower back is at least 4 inches.

43. A belt for increasing comfort and reducing back pain while lying down, comprising:
   a flexible padded belt for supporting only a wearer's midsection, said midsection located generally between said wearer's hips and lower chest, while said wearer is lying in a substantially horizontal position;
   said flexible padded belt sized to encircle the wearer's lower back, side and stomach regions;
   said flexible padded belt having padding, said padding extending along a substantial length of the belt, of a firmness and thickness sufficient to maintain the wearer's lower back in a substantially straight posture when said belt is situated between said wearer's side and a substantially horizontal lying surface and sufficient to maintain the natural hollow of the wearer's lower back region when said belt is situated between said wearer's lower back region and a substantially horizontal lying surface; and
   said flexible padded belt having two ends, said ends further having fastening means for holding said flexible padded belt in a position encircling the wearer's lower back, side and stomach regions without leaving significant excess unsecured length, wherein
   said flexible padded belt further has a contact face and an outer face;
   said flexible padded belt, when said ends are fastened, forms a shape that is capable of surrounding the wearer's lower back, side and stomach regions with the contact face and the outer face both remaining substantially parallel to the wearer's skin surface and to each other; and
   the uncompressed thickness of said padding in the portions of said belt intended to contact the wearer's sides and lower back is at least 1 inch.

44. The belt of claim 43 wherein the uncompressed thickness of said padding in the portions of said belt intended to contact the wearer's sides and lower back is at least 1½ inches.

45. The belt of claim 43 wherein the uncompressed thickness of said padding in the portions of said belt intended to contact the wearer's sides and lower back is at least 2 inches.

46. The belt of claim 43 wherein the uncompressed thickness of said padding in the portions of said belt intended to contact the wearers sides and lower back is at least 2½ inches.

47. The belt of claim 43 wherein the uncompressed thickness of said padding in the portions of said belt intended to contact the wearer s sides and lower back is at least 3 inches.

48. The belt of claim 43 wherein the uncompressed thickness of said padding in the portions of said belt intended to contact the wearer's sides and lower back is at least 3½ inches.

49. The belt of claim 43 wherein the uncompressed thickness of said padding in the portions of said belt intended to contact the wearer's sides and lower back is at least 4 inches.

50. A belt for increasing comfort and reducing back pain while lying down, comprising:
   a flexible padded belt for supporting only a wearer's midsection, said midsection located generally between said wearer's hips and lower chest, while said wearer is lying in a substantially horizontal position;
   said flexible padded belt sized to encircle the wearer's lower back, side and stomach regions;
   said flexible padded belt having padding, said padding extending along a substantial length of the belt, of a firmness and thickness sufficient to maintain the wearer's lower back in a substantially straight posture when said belt is situated between said wearer's side and a substantially horizontal lying surface and sufficient to maintain the natural hollow of the wearer's lower back region when said belt is situated between said wearer's lower back region and a substantially horizontal lying surface; and said flexible padded belt having two ends, said ends further having fastening means for holding said flexible padded belt in a position encircling the wearer's lower back, side and stomach regions without leaving significant excess unsecured length, wherein said flexible padded belt can encircle the wearer's lower back, side and stomach regions without any significant twisting of the belt along its lengthwise dimension; and the uncompressed thickness of said padding in the portions of said belt intended to contact the wearer's sides and lower back is at least 1 inch.

51. The belt of claim 50 wherein the uncompressed thickness of said padding in the portions of said belt intended to contact the wearer's sides and lower back is at least 1½ inches.

52. The belt of claim 50 wherein the uncompressed thickness of said padding in the portions of said belt intended to contact the wearer's sides and lower back is at least 2 inches.

53. The belt of claim 50 wherein the uncompressed thickness of said padding in the portions of said belt intended to contact the wearer's sides and lower back is at least 2½ inches.

54. The belt of claim 50 wherein the uncompressed thickness of said padding in the portions of said belt intended to contact the wearer's sides and lower back is at least 3 inches.

55. The belt of claim 50 wherein the uncompressed thickness of said padding in the portions of said belt intended to contact the wearer's sides and lower back is at least 3½ inches.

56. The belt of claim 50 wherein the uncompressed thickness of said padding in the portions of said belt intended to contact the wearer's sides and lower back is at least 4 inches.

* * * * *